United States Patent [19]

Brokowski et al.

[11] Patent Number: 4,926,692
[45] Date of Patent: May 22, 1990

[54] METHOD OF MEASUREMENT OF RESIDUAL STRESSES IN THE MATERIAL OF THE OBJECT UNDER TEST

[75] Inventors: Andrzej Brokowski; Julian Deputat; Krzysztof Mizerski, all of Warsaw, Poland

[73] Assignee: Polska Akademia Nauk Instytut Podstrowowych Problemow, Warsaw, Poland

[21] Appl. No.: 268,662

[22] Filed: Nov. 4, 1988

Related U.S. Application Data

[63] Continuation of Ser. No. 35,064, Apr. 6, 1987, abandoned.

[30] Foreign Application Priority Data

Apr. 18, 1986 [PL] Poland .................................. 259038

[51] Int. Cl.$^5$ ........................................... G01N 29/00
[52] U.S. Cl. ..................................................... 73/597
[58] Field of Search .......................... 73/640, 644, 597

[56] References Cited

U.S. PATENT DOCUMENTS

| | | | |
|---|---|---|---|
| 3,720,098 | 3/1973 | Dixon | 73/597 |
| 3,812,709 | 5/1974 | Benson et al. | 73/597 |
| 3,978,712 | 9/1976 | Cowan et al. | 73/644 |
| 4,121,467 | 10/1978 | Gerhart | 73/597 |
| 4,462,257 | 7/1984 | Gerhart et al. | 73/644 |
| 4,522,071 | 6/1985 | Thompson | 73/597 |

FOREIGN PATENT DOCUMENTS

0681366  8/1979  U.S.S.R. .................................. 73/597

OTHER PUBLICATIONS

B. E. Gordon, Jr., "Measurement of Applied and Residual Stresses Using an Ultrasonic Instrumentation System", ISA Transactions, vol. 19, No. 2.
Clark, A. V. Jr., Fukuoka, H., Mitrakovic, D. V., Moulder, J. C., "Characterization of Residual Stress and Texture in Coast Steel Railroad Wheels", Ultrasonic, 1986, vol. 24, pp. 281–288.
Thompson, R. B., Lee, S. S., and Smith, J. F., "Angular Dependence of Ultrasonic Wave Propagation in a Stressed Orthorhombic Continuum", Theory and Application to the Measurement of Stress and Texture, JASA, vol. 80, Sep. 1986, pp. 921–931.

*Primary Examiner*—Michael J. Tokar
*Assistant Examiner*—Mark A. Spector
*Attorney, Agent, or Firm*—Ladas & Parry

[57] ABSTRACT

The invention solves the problem of measurement of internal stresses in cylindrical objects, such as axles, shafts and tubes made of material with varying non-uniform homogeneous mechanical properties. The method consists in that a beam of ultrasonic waves is thrown onto the surface of a cylindrical object being tested, said beam being refracted at an angle of 90 degrees. Next the times of passage for every type of waves are measured. On the basis of the calculated differences of the times of passage with a standard the absolute values of components of stresses are calculated. The method is applicable for non-destructive testing of properties and structure of materials and products.

5 Claims, 7 Drawing Sheets

1

METHOD OF MEASUREMENT OF RESIDUAL STRESSES IN THE MATERIAL OF THE OBJECT UNDER TEST

"This is a continuation of co-pending application Ser. No. 07/035,064 filed on Apr. 6, 1987, now abandoned". (See XVIII below)

BACKGROUND OF THE INVENTION

This invention relates to a method of measuring residual stresses in the material of an object and, particularly, in an object having a curved surface accessible from one side only.

Those skilled in the art know a method of ultrasonic measurement of stresses in the material of an object under test from Polish patent publication No. 235,656. According to that method, beams of two types of ultrasonic waves are propagated in the material of the object parallel to a surface of the object. The travel times of pulses of these two types of ultrasonic subsurface waves over a known path in the material of the object under test and in a reference material are measured. Next, the absolute values of stresses in the material of the object under test are calculated from the differences of the travel times.

This known method of ultrasonic measurement of stresses and the equipment for implementation thereof enable the values of longitudinal components of residual stresses to be determined in the objects with plane surfaces. The described method is not applicable to objects with curved surfaces.

SUMMARY OF THE INVENTION

The aim of the invention is, therefore, development of a method of non-destructive measurement of stresses in the material of an object having a curved, e.g. cylindrical surface subjected to a two-dimensional, i.e. planar state of stress, a curved surface of sufficiently large radius of curvature being a flat surface, as used herein.

In the method according to the invention, beams of three types of ultrasonic waves are propagated across a measuring zone of a curved-surface (including flat), e.g. cylindrical object to be tested. Specifically, the three types of ultrasonic waves are surface (i.e. Rayleigh) and longitudinal and transverse subsurface waves propagated in the same direction along one line (e.g. the generatrix) across the measuring zone. Next, the travel times of the longitudinal and transverse, subsurface and surface waves over a definite distance, defined by a differential probe set, for example, along the line are determined. Finally, the absolute values of the components of stresses in the material under test in the direction of the propagation of the three types of ultrasonic waves and in the direction perpendicular thereto are calculated from the differences of the travel times of the ultrasonic waves in the material of the object under test and in a reference material. Preferably, the travel times in the material of the object and the reference material are determined with the same probe set.

The method according to the invention thus makes possible measurements of the plane states of stress in flat or cylindrical objects.

DESCRIPTION OF THE DRAWING

An example of the method will now be described with reference to a drawing, wherein.

EXAMPLE OF METHOD

Figure 1:
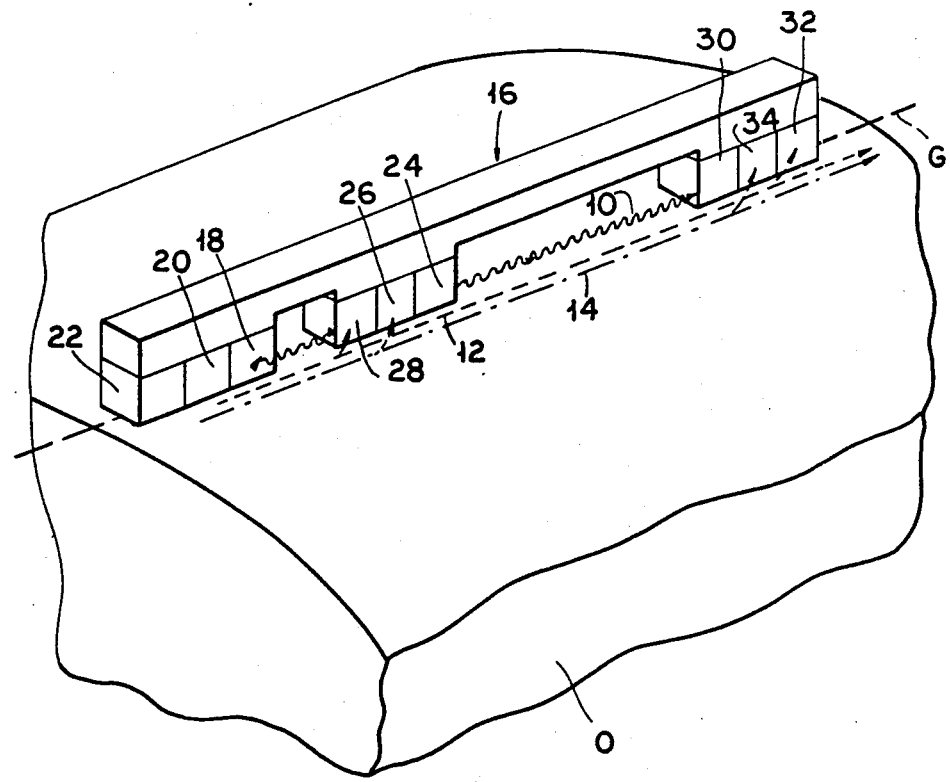
FIG. 1 is a schematic perspective view of a probe set for the method on an object.

In general, as shown in FIG. 1, travel times of surface (R) and longitudinal (L) and transverse (T) subsurface ultrasonic waves 10, 12, 14, respectively, propagated along the generatrix G of a cylinder of material of an object 0 to be tested over a path length determined by a differential probe set at 16 are measured. Longitudinal and circumferential stress components ($\delta_L$ and $\delta_\theta$ in Equation 1 hereafter) are calculated from these measurements and the values of elastoacoustic constants ($\beta_{R\parallel}$, $\beta_{R\perp}$, $\beta_{L\parallel}$ and $B_{L\perp}$ in Equations 1 and 2 hereafter) determined experimentally for the material and the respective wave travel times ($t_R^\omega$, $t_L^\omega$ and $t_T^\omega$ in Equations 3 and 4 hereafter) in a separate, standard or reference object made of the same grade of material, but not stressed.

Figure 7:
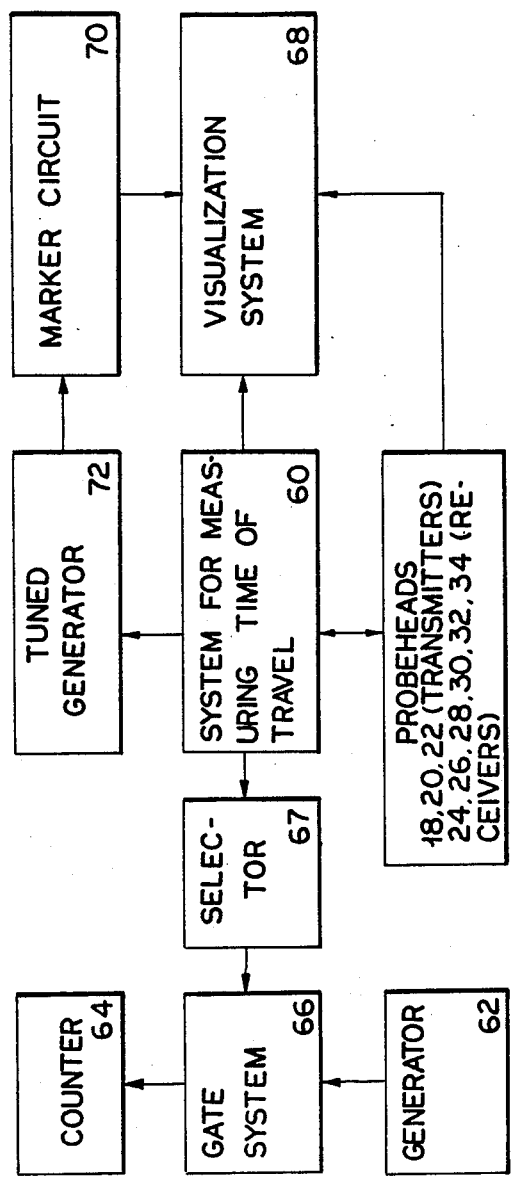
FIG. 7 is a schematic of measuring devices connected to the probe set of FIG. 1.

Beams of the ultrasonic waves 10, 12, 14 are produced by a corresponding set of ultrasonic-wave transmitting probe heads 18, 20, 22, respectively, in the probe set at 16 and contact coupled with the object 0 under test and received by two complementary sets of receiving probe heads 24, 26, 28 and 30, 32, 34, respectively, connected to the measuring system of ultrasonic equipment (FIG. 7). The beams of ultrasonic waves 10, 12, 14 propagate parallel to the surface of the object 0 under test as surface and longitudinal and transverse subsurface waves, respectively.

Figure 2:
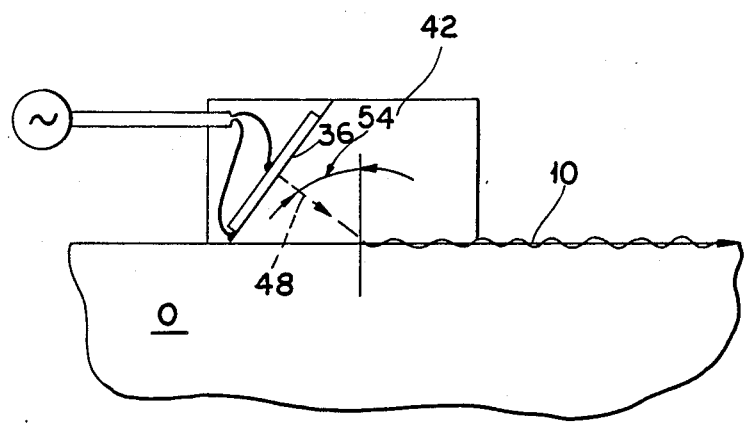
FIG. 2 is a schematic elevation of a portion of the probe set shown in FIG. 1.
Figure 3:
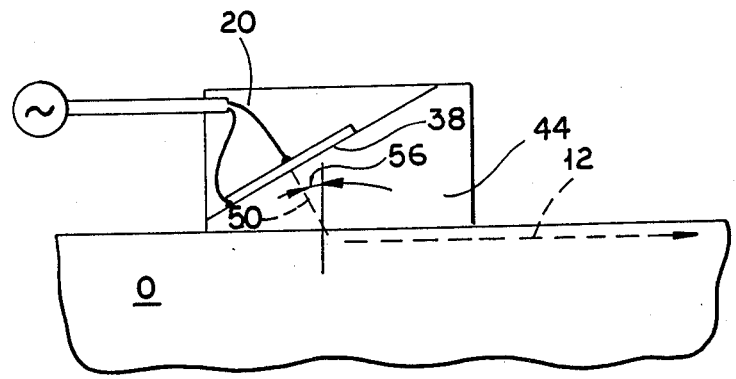
FIG. 3 is a schematic elevation of another portion of the probe set shown in FIG. 1.
Figure 4:
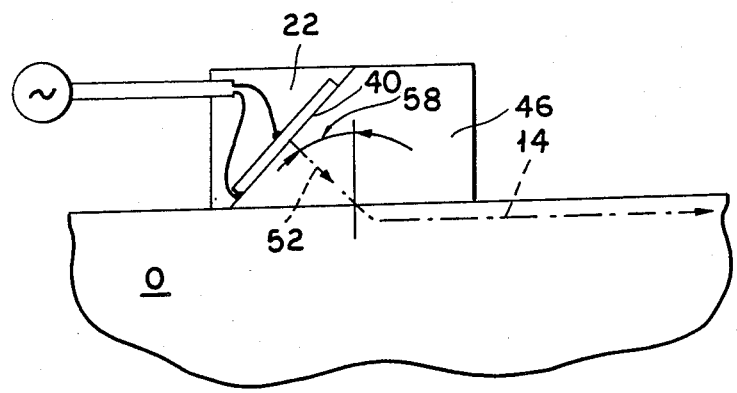
FIG. 4 is a schematic elevation of still another portion of the probe set shown in FIG. 1.

The ultrasonic-wave transmitting probe heads 18, 20, 22 for the surface and longitudinal and transverse subsurface waves, respectively, are shown in further detail in FIGS. 2, 3, 4, respectively. In each, ultrasonic waves 48, 50, 52 are produced by a piezoelectric transducer 36, 38, 40 in a block 42, 44, 46, for example of plastic, at an angle to transmit the ultrasonic waves 48, 50, 52 at a critical angle 54, 56, 58 to a surface of the block on the surface of the object 0. The piezoelectrically-transduced ultrasonic waves 48, 50, 52 are refracted thereat into the surface and longitudinal and transverse ultrasonic waves 10, 12, 14, respectively, in the object 0 according to their critical angles 54, 56, 58 and velocities according to Snell's Law.

Figure 5:
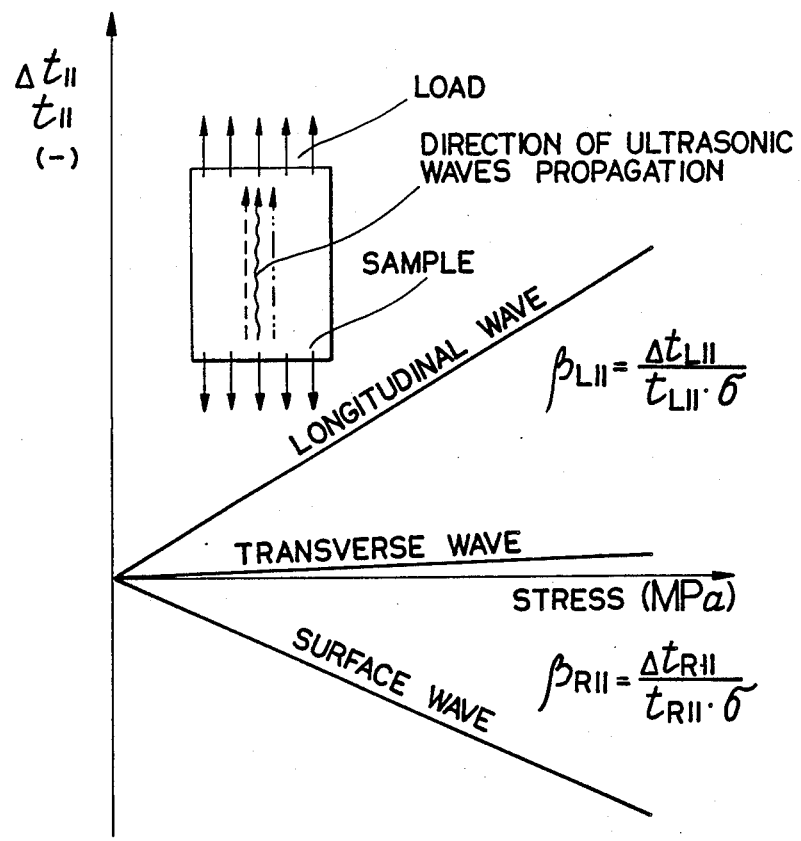
FIG. 5 is a graphical solution of wave-parallel elastoacoustic constants for a material.
Figure 6:
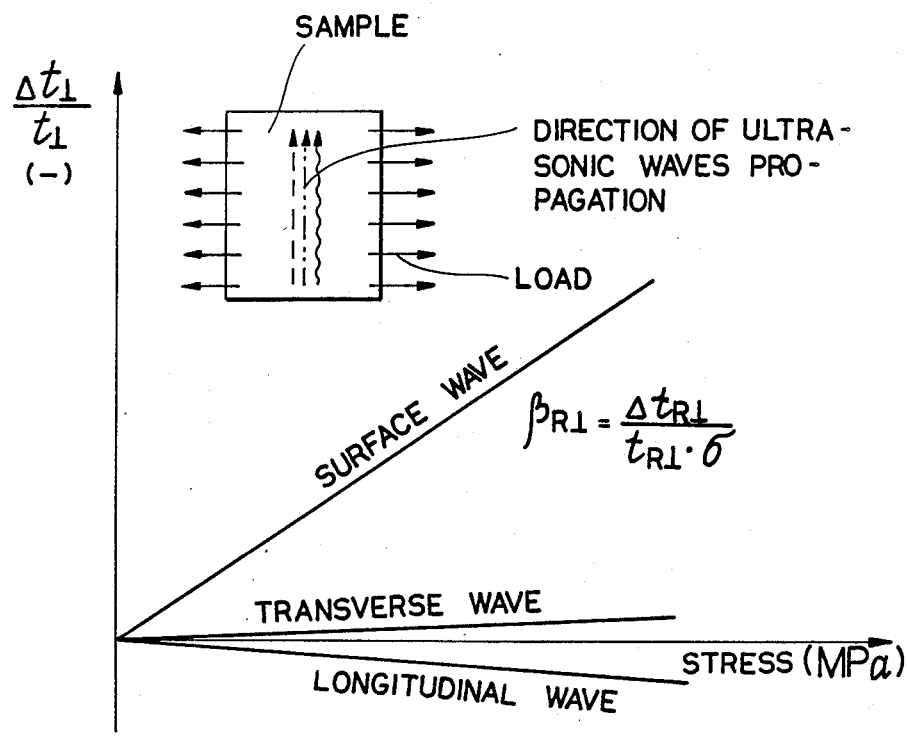
FIG. 6 is a graphical solution of wave-perpendicular elastoacoustic constants for the material of FIG. 5.

The produced waves 10, 12, 14 are affected by various values of elastoacoustic constants, $\beta_{R\parallel}$, $\beta_{L\parallel}$, $\beta T_\parallel$ and $\beta_{R\perp}$, $\beta_{L\perp}$, $\beta_{T\perp}$ for the surface and longitudinal and transverse subsurface waves with parallel ($\parallel$) and transverse ($\perp$) stress, respectively, as shown in FIGS. 5 and 6. That is, their velocity of propagation depends to a different extent upon the direction of stress (load) in the kind of material of the object 0. The travel time for each type of ultrasonic wave 10, 12, 14 thus is measured in a differential system by the set of ultrasonic probe heads at 16 including the set of transmitting heads 18, 20, 22 and two sets of receiving heads 24, 26, 28 and 30, 32, 34 situated at different distances from the transmitting heads along a straight line to define a single zone of the material of the object 0 under test.

As shown in FIG. 7, the receiving probe heads 24, 26, 28 and 30, 32, 34 are connected to a measuring system, which includes a time meter, i.e. system for measurement of times of travel of ultrasonic pulses 60. The system for multiplication of the travel times is provided, as well as a standard- or clock-pulse generator 62 with a counter 64 connected thereto via a gate system 66 controlled by a selector 67. Said counter counts the number of standard pulses during the time equal to multiple of times of travel of ultrasonic pulses between the respective transmitting and receiving head.

The system 60 for measurement of travel times is also provided with a system 68 for visualization of the ultrasonic pulses, as well as with a marker circuit 70 via a tuned generator 72 of rectangular pulses with the duration so suited as to obtain a V-shaped pulse. The marker circuit is connected to the system 68 for visualization of the ultrasonic pulses in such a way as to obtain addition of those pulses.

An accurate measurement of the travel time of the waves with simultaneous visualization of the received pulse and precise setting of the time marker on the spot from which the time is to be measured enables the individual differences of the acoustic properties of the material of the object being tested to be taken into account.

In consequence, the method according to the invention makes possible measurements of absolute values of stresses. For surface and subsurface longitudinal waves propagating in the direction of the generatrix, we have the following relationships:

$$t_R = t_R^o(1 + \beta_{R\|}\delta_L + \beta_{R\perp}\delta_\theta)^{-1} \quad (1)$$

$$t_L = t_L^o(1 + \beta_{L\|}\delta_L + \beta_{L\perp}\delta_\theta)^{-1} \quad (2)$$

where:

$t_R$-travel time of surface waves propagating in the object under test;

$t_R^o$-travel time of surface waves which would propagate in the material under test if it has no internal stresses, in the same measuring zone;

$t_L$-travel time of subsurface longitudinal wave in the material of the object under test;

$t_L^o$-travel time of subsurface longitudinal wave in the material under test if it has no stresses, in the same measuring zone;

$\beta_{R\|}$, $\beta_{L\|}$-electroacoustic constants for the grade of material under test for surface and longitudinal waves respectively, propagating in a direction parallel to the direction of stress.

$\beta_{R\perp}$, $\beta_{L\perp}$-elastoacoustic constants for the grade of material under test for surface and longitudinal waves respectively, propagating in a direction perpendicular to the direction of stress.

$\delta_L$-component of stress in the direction of ultrasonic waves propagation $\delta_\theta$-component of stress in the direction of perpendicular to the ultrasonic waves propagation.

Travel time of the subsurface transverse waves propagating in the direction of generatrix and, polarized, in the surface direction perpendicular thereto does not depend upon stresses, so that it may be assumed that $t_T = t_T^o$.

The differences of the travel times of the surface and longitudinal and transverse subsurface waves propagating in a non-stressed reference material and in the same material of the object under test then may be expressed by:

$$t_L^o - t_L^\omega = K_L(t_T - t_T^\omega) \quad (3)$$

$$t_R^o - t_R^\omega = K_R(t_T - t_T^\omega) \quad (4)$$

where $t_T$ is the travel time of subsurface transverse wave in the material of the object being tested, $t_T^\omega$-travel time of subsurface transverse wave in the material of a standard without any internal stresses, $t_L^\omega$-travel time of subsurface longitudinal waves in the material of a standard without any internal stresses, $t_R^\omega$-travel time of surface wave in the material of standard without any internal stresses.

From relationships (1) and (2), taking also into account the values of $t_L^o$ and $t_R^o$ calculated from the relationships (3) and (4), it is possible to calculate the values of stresses $\delta_L$ and $\delta_Q$ parallel and perpendicular to the direction of ultrasonic wave propagation:

$$\sigma_L = \frac{\beta_{L\perp}t_L(t^o_R - t_R) - \beta_{R\perp}t_R(t^o_L - t_L)}{(\beta_{R\|}\beta_{L\perp} - \beta_{R\perp}\beta_{L\|})t_R t_L} \quad (5)$$

$$\sigma_\theta = \frac{\beta_{R\|}t_R(t^o_L - t_L) - \beta_{L\|}t_L(t^o_R - t_R)}{(\beta_{R\|}\beta_{L\perp} - \beta_{R\perp}\beta_{L\|})t_R t_L} \quad (6)$$

The method has been used for the measurement of residual stresses in a heat treated cylindrical object. With a known meter, the travel times of surface and longitudinal and transverse subsurface ultrasonic waves over a path of definite length defined by the probe set at 16 along the generatrix of the cylindric object 0 have been measured. Moreover, measurements of the travel times of the surface and longitudinal and transverse subsurface waves over a path of the same length have also been performed on a non-stressed, reference material, for example steel, of the same grade as that of the cylindrical object under test. From other specimens made of the same grade of steel, the values of the elastoacoustic constants have also been determined for the individual modes of waves propagating in the direction of a stress and in the direction perpendicular to the direction of the stress, as have the constants of proportionality between the variations of travel times for the surface and longitudinal and transverse subsurface waves. All values of the travel times have been at a temperature of 18 degrees Centigrade.

The following data have been obtained:

Results of measurements for a cylindrical object being tested:

$t_L = 33820$ ns
$t_T = 61554$ ns
$t_R = 64823$ ns

Results of measurements for the reference or standard:

$t_L^\omega = 33685$ ns
$t_R = 61581$ ns
$t_R^\omega = 65276$ NS

Elastoacoustic constants of the material:

$\beta_{L\|} = -1.24 \times 10^{-5}$ MPa$^{-1}$
$\beta_{L\perp} = 0.10 \times 10^{-5}$ MPa$^{-1}$
$\beta_{R\|} = 0.87 \times 10^{-5}$ MPa$^{-1}$
$\beta_{R\perp} = -1.27 \times 10^{-5}$ MPa$^{-1}$ Constants of Proportionality:

$K_L = 0.55$
$K_R = 1.06$

Values of the travel times of longitudinal and surface waves calculated from the relationship 3 and 4, corresponding to the non-stressed material of the object under test are as follows:

$$t_L^o = 33685 - 0.55/61554 - 61581/ = 33700 \text{ ns}$$

$$t_R^o = 65276 - 1.06/61554 - 61581/ = 65305 \text{ ns}$$

After having substituted these values into formulae 5 and 6, we obtain: $\delta_L = 253$ MPa, $\delta_\theta = -412$ MPa.

Instead of the relationships (1) and (2) which were used in the example described above, one may also use the relationships for longitudinal and tranverse waves propagating in the direction of the generatrix of a cylinder (2) and the relationship (7) for the surface waves propagating over the circumference of a cylinder:

$$t_{R\theta} = t_{R\theta}^o (1 + \beta_{R\parallel} \delta_\theta + \beta_{R\perp} \delta_L)^{-1} \quad (7)$$

where: $t_{R\theta}$-travel time of surface wave over a distance determined by probe set construction along the circumference of the cylinder under testing;

$t_{R\theta}$-a travel time of surface wave over the same distance along the circumference of the cylinder without stresses.

We claim:

1. A method of measuring residual stresses in the material of an object, comprising:
   propagating surface and longitudinal and transverse subsurface ultrasonic waves in the material of an object in the same direction along one line parallel to a surface of the object;
   detecting the travel times of the waves over a path length along the line of the object and a path of the same length in a standard of the same grade of material as the object;
   determining experimentally the elastoacoustic constants and constants of proportionality for the material of the object; and
   calculating residual stress components parallel and perpendicular to the direction of propagation of the waves from the travel times and constants.

2. A method of determining stresses components in an object comprising:
   generating successively pulses of subsurface longitudinal, subsurface transverse and surface waves, said waves propagating along one line in the same direction parallel to the surface of material, said waves are produced by three ultrasonic transmitting probeheads coupled to the material, said transmitting probeheads are arranged along one line, said waves are produced successively in material of standard and in material of object under test;
   detecting of said waves by means of six receiving probeheads arranged on one line with said transmitting probeheads, said receiving probeheads are situated on the beginning and on the end of measuring zone of said standard and said material under test,
   determining of the differential times of travel of pulses of said three types of waves between said receiving probeheads, said times of travel are determined on said material of standard and on material said object under test;
   calculating of stress components from differences between said times of travel of pulses of said waves measured on said standard material and said object under test.

3. The method of claim 2, wherein said standard and said object under test are made from the same grade of material and said standard has no internal stresses.

4. The method of claim 2, wherein said times of travel of said pulses are measured by a system for measurement of the times of travel of the ultrasonic pulses provided with a standard-pulse generator with a counter connected thereto via gate system controlled by a selector, said counter counting the number of standard pulses during the times of travel of several of said ultrasonic pulses between said respective transmitting and receiving probeheads, said system for measurement of the times of travel being connected with a system of visualization of said ultrasonic pulses, as well as with a marker circuit via a tuned generator of pulses with a duration so short as to be V-shaped, said marker circuit being connected to the system for visualization of said ultrasonic pulses.

5. A differential probe set, comprising:
   a set of three transmitting probeheads for respectively simultaneously propagating surface and longitudinal and transverse subsurface ultrasonic waves in materials of an object and a reference, the waves being propagated in he materials in the same direction along respective lines on the materials; and
   two sets of three receiving probeheads each, the three receiving probeheads of each set being for respectively receiving the surface and longitudinal and transverse subsurface ultrasonic waves propagated by the three transmitting probeheads, the two sets of the three receiving probeheads being spaced from each other and the set of three transmitting probeheads along the lines on the object and reference when the set of transmitting probeheads propagate the waves in the materials thereof.

* * * * *